(12) United States Patent
Matsushita

(10) Patent No.: US 8,908,173 B2
(45) Date of Patent: Dec. 9, 2014

(54) HIGH-FREQUENCY POWER SUPPLY FOR PLASMA AND ICP OPTICAL EMISSION SPECTROMETER USING THE SAME

(71) Applicant: Shimadzu Corporation, Kyoto (JP)

(72) Inventor: Tomoyoshi Matsushita, Kyoto (JP)

(73) Assignee: Shimadzu Corporation, Kyoto-shi, Kyoto (JP)

( * ) Notice: Subject to any disclaimer, the term of this patent is extended or adjusted under 35 U.S.C. 154(b) by 0 days.

(21) Appl. No.: 14/017,155

(22) Filed: Sep. 3, 2013

(65) Prior Publication Data
US 2014/0071448 A1  Mar. 13, 2014

(30) Foreign Application Priority Data
Sep. 11, 2012 (JP) ................................. 2012-199251

(51) Int. Cl.
| | |
|---|---|
| G01J 3/30 | (2006.01) |
| H05H 1/28 | (2006.01) |
| G01N 21/73 | (2006.01) |
| H05H 1/30 | (2006.01) |
| H05H 1/46 | (2006.01) |
| G01N 21/68 | (2006.01) |

(52) U.S. Cl.
CPC ................. H05H 1/28 (2013.01); G01N 21/73 (2013.01); H05H 1/30 (2013.01); H05H 1/46 (2013.01); G01N 21/68 (2013.01); H05H 2001/4667 (2013.01)
USPC ........................................................ 356/316

(58) Field of Classification Search
USPC ........................................................ 356/316
See application file for complete search history.

(56) References Cited

U.S. PATENT DOCUMENTS

| | | | |
|---|---|---|---|
| 6,682,630 B1 * | 1/2004 | Colpo et al. ............. | 156/345.48 |
| 2012/0277515 A1 * | 11/2012 | Lemont et al. ................ | 588/311 |

FOREIGN PATENT DOCUMENTS

JP   11-101748 A   4/1999

* cited by examiner

*Primary Examiner* — Abdullahi Nur
(74) *Attorney, Agent, or Firm* — McDermott Will & Emery LLP

(57) ABSTRACT

In a high-frequency power supply for plasma having a housing and a high-frequency circuit substrate placed inside the housing, elements for supplying a high-frequency current to a high-frequency inductive coil are mounted on the high-frequency circuit substrate, a cooling block for cooling the high-frequency circuit substrate is provided, and a coolant path a for allowing a coolant to flow through is formed inside the cooling block so that the coolant is allowed to flow through the coolant path when a high-frequency current is supplied and the coolant is not allowed to flow through the coolant path when a high-frequency current is not supplied.

10 Claims, 3 Drawing Sheets

HIGH-FREQUENCY POWER SUPPLY FOR PLASMA AND ICP OPTICAL EMISSION SPECTROMETER USING THE SAME

TECHNICAL FIELD

The present invention relates to a high-frequency power supply for plasma and an ICP optical emission spectrometer using the same.

BACKGROUND ART

In an ICP optical emission spectrometer, a sample is introduced into a plasma flame so as to emit light through excitation. The thus-emitted light is dispersed through a grating so as to be detected by a photodetector, and as a result, an emission spectrum is acquired. In addition, an element contained in the sample is qualitatively analyzed by the type of wavelength in the spectrum line (bright line spectrum) that appears in the emission spectrum, and furthermore, the element is quantitatively analyzed by the intensity of this bright line spectrum (see Patent Document 1).

FIG. 3 is a schematic diagram showing the structure of an example of a conventional ICP optical emission spectrometer. An ICP optical emission spectrometer 200 is provided with a plasma torch 18 for optical emission spectrometry from which a plasma flame 22 is generated, a sample gas-supplying unit 44, a plasma gas-supplying unit 41, a cooling gas-supplying unit 42, a light measuring unit 43 for detecting the emitted light, a high-frequency power supply 130 for plasma that supplies a high-frequency current I, and a computer (control unit) 150 for controlling the entirety of the ICP optical emission spectrometer 200.

The plasma torch 18 for optical emission spectrometry is provided with a sample gas tube 11 in cylindrical form, a plasma gas tube 12 in cylindrical form that covers the outer periphery of the sample gas tube 11 with a space in between, a coolant gas tube 13 in cylindrical form that covers the outer periphery of the plasma gas tube 12 with a space in between, and a high-frequency inductive coil 21 with two to three loops around the end portion of the outer periphery of the coolant gas tube 13.

The plasma gas-supplying unit 41 allows argon gas to flow in the upward direction at a relatively low speed between the outer periphery of the sample gas tube 11 and the inner periphery of the plasma gas tube 12. As a result, argon gas is jetted from the upper end portion of the flow path created between the outer periphery of the sample gas tube 11 and the inner periphery of the plasma gas tube 12. When the jetted argon gas is ionized by the electrons that have been accelerated by the high-frequency electromagnetic field created by the high-frequency inductive coil 21, argon cations and electrons are generated. The generated electrons further collide with argon so as to proliferate the ionization, and thus, a stable plasma flame 22 is generated in the upper end portion.

The cooling gas-supplying unit 42 allows the argon gas to flow in the upward direction at a relatively high speed between the outer periphery of the plasma gas tube 12 and the inner periphery of the coolant gas tube 13. As a result, argon gas is jetted from the upper end portion of the flow path created between the outer periphery of the plasma gas tube 12 and the inner periphery of the coolant gas tube 13, and the thus-jetted argon gas flows in the upward direction along the outside of the plasma flame 22 that has been generated in the upper end portion.

When a sample is analyzed, the sample and the argon gas are made to flow in the upward direction through the space surrounded by the inner periphery of the sample gas tube 11. The sample is jetted from the end portion of the sample gas tube 11 together with the argon gas so as to be introduced into the plasma flame 22. As a result, a compound included in the sample makes contact with the plasma flame 22 and is converted to an atom or is ionized so as to emit light through excitation.

The light measuring unit 43 has a housing 43a, a condenser lens 43b for introducing the light emitted from the plasma torch 18 for optical emission spectrometry into the housing 43a, a grating 43c for dispersing the emitted light, and a photodetector 43d for detecting the emission spectrum.

The computer 150 is formed of a CPU 151 and input apparatuses 52, such as a keyboard and a mouse, and carries out a qualitative analysis on an element contained in the sample on the basis of the type of wavelength of the bright light spectrum in the emission spectrum detected by the photodetector 43d, and furthermore carries out a quantitative analysis on the element on the basis of the intensity of the bright light spectrum.

The above-described ICP optical emission spectrometer 200 is provided with a high-frequency power supply 130 for plasma that supplies a high-frequency current I to the high-frequency inductive coil 21. The plasma high-frequency power supply 130 is provided with a housing 131 having openings 131a and 131b, a high-frequency circuit substrate 32 placed inside the housing 131, and a cooling fan 133 placed in proximity to the opening 131a of the housing 131.

The housing 131 is in rectangular parallelepiped form having a space inside (50 cm×20 cm×35 cm, for example) where the opening 131a is created at the bottom while the opening 131b is created at the top.

Various elements (transistors and large-scale capacitors, for example) for supplying a high-frequency current I to the high-frequency inductive coil 21 are mounted on the upper surface of the high-frequency circuit substrate 32 in plate form.

The cooling fan 133 allows air to flow from the opening 131a of the housing 131 to the opening 131b of the housing 131 through the inside of the housing 131 when rotating.

In the thus-formed high-frequency power supply 130 for plasma, elements on the high-frequency circuit substrate 32 emit heat when a high-frequency current I is supplied, and therefore, the cooling fan 131 is rotated so as to allow air to flow, and thus, the heat generated from the elements on the high-frequency circuit substrate 32 is radiated.

In some other ICP optical emission spectrometers, a matching box is provided between the high-frequency power supply 130 for plasma and the high-frequency inductive coil 21 so as to form a structure for reducing the waves reflected from the high-frequency inductive coil 21, and the impedance is matched by changing the capacitance by means of the matching box.

PRIOR ART DOCUMENT

Patent Document

Patent Document 1: Japanese Unexamined Patent Publication H11 (1999)-101748

SUMMARY OF THE INVENTION

Problem to be Solved by the Invention

A number of transistors and large-scale capacitors are mounted on the upper surface of the high-frequency circuit substrate 32 in plate form in the above-described ICP optical emission spectrometer 200, which also has amplifying circuits in multiple stages, and therefore is costly and large.

The present inventor examined the high-frequency power supply for plasma with which reduction in the size and cost could be achieved. First, the control system of the high-frequency power supply was switched from the conventional capacitance-tuning system with a fixed frequency, where a number of transistors and large-scale capacitors were mounted, to a self-oscillation system, and a power MOSFET and a compact ceramic capacitor, which were mounted on the upper surface of a high-frequency circuit substrate, were fabricated. In the case of the self-oscillation system, it is necessary for the path through which a high-frequency current flows to be patterned as the shortest by using a power semiconductor element in order to reduce the power loss due to the inductance of the path of the high-frequency current, which leads to a reduction in the scale of the system.

However, the heat density (the amount of heat emissions) of each element increased, and cooling by the cooling fan, which allows the air to flow, became insufficient. Therefore, it was determined to use a cooling block made of a metal (made of copper, for example) where cooling water (coolant) flows through the inside instead of the use of a cooling fan for allowing the air to flow.

The inside of the housing of the high-frequency power supply for plasma becomes of a high temperature (35° C., for example) because the elements on the high-frequency circuit substrate emit heat when the plasma is turned on (when a high-frequency current is supplied). However, when the plasma is turned off (when no high-frequency current is supplied), the elements on the high-frequency circuit plate do not emit heat, and therefore, the elements on the high-frequency circuit substrate are cooled too much when the coolant in the cooling block (5° C. to 30° C., for example) is used for cooling. FIG. 2 is a graph showing an air line diagram. As shown in FIG. 2, the dew point temperature for 70% humidity is 28.7° C., and therefore, the moisture in the air forms dew, which short circuits and breaks an element on the high-frequency circuit substrate, when the element on the high-frequency circuit substrate has been cooled to the dew point temperature or lower.

Means for Solving Problem

The present inventor found a way according to which cooling water flows through the inside of the cooling block when the plasma is turned on and no cooling water flows through the inside of the cooling block when the plasma is turned off.

That is to say, the high-frequency power supply for plasma according to the present invention is provided with a housing, a high-frequency circuit substrate placed inside the housing, and a cooling block for cooling the high-frequency circuit substrate. Elements for supplying a high-frequency current to a high-frequency inductive coil are mounted on the high-frequency circuit substrate of the high-frequency power supply for plasma, and a coolant path for allowing a coolant to flow through is formed inside the cooling block in such a manner that the coolant flows through the coolant path when a high-frequency current is supplied, while no coolant flows through the coolant path when a high-frequency current is not supplied.

Effects of the Invention

As described above, the high-frequency power supply for plasma according to the present invention can prevent condensation, and thus can prevent the elements on the high-frequency circuit substrate from being short-circuited.

(Other Means for Solving Problem and Effects of the Invention)

In the above-described high-frequency power supply for plasma according to the invention, the inside of the housing may be sealed airtight.

When the inside of the housing of the high-frequency power supply for plasma according to the present invention is an airtight space, dust can be prevented from entering into the housing, and therefore, the elements on the high-frequency circuit substrate can be prevented from being short-circuited, unlike a case where dust enters through an opening of the housing together with air, and the dust adheres to an element on the high-frequency circuit substrate so as to short circuit and break the element.

In addition, the above-described high-frequency power supply for plasma according to the invention may be provided with a switching mechanism that makes the switching between the above-described coolant path and a bypass placed outside the housing possible so that the coolant flows through the coolant path when a high-frequency current is supplied, and the current flows through the bypass when a high-frequency current is not supplied.

In addition, the high-frequency power supply for plasma according to the present invention may be provided with a high-frequency power supply for plasma as described above, a plasma torch having a high-frequency inductive coil, a light-measuring unit for detecting emitted light, and a control unit for analyzing an element by generating a plasma flame using the above-described plasma torch and introducing a sample into the plasma flame.

Furthermore, in the above-described ICP optical emission spectrometer according to the invention, the above-described control unit may control the system in such a manner that the coolant flows through the coolant path when a high-frequency current is supplied and the coolant does not flow through the coolant path when a high-frequency current is not supplied.

In the ICP optical emission spectrometer according to the present invention, the control unit automatically operates in sync with the turning on/off of plasma.

PREFERRED EMBODIMENT OF THE INVENTION

In the following, a preferred embodiment of the present invention is described in reference to the drawings. Here, the present invention is not limited to the embodiment described in the following, but includes various modifications as long as the gist of the present invention is not deviated from.

Figure 1:
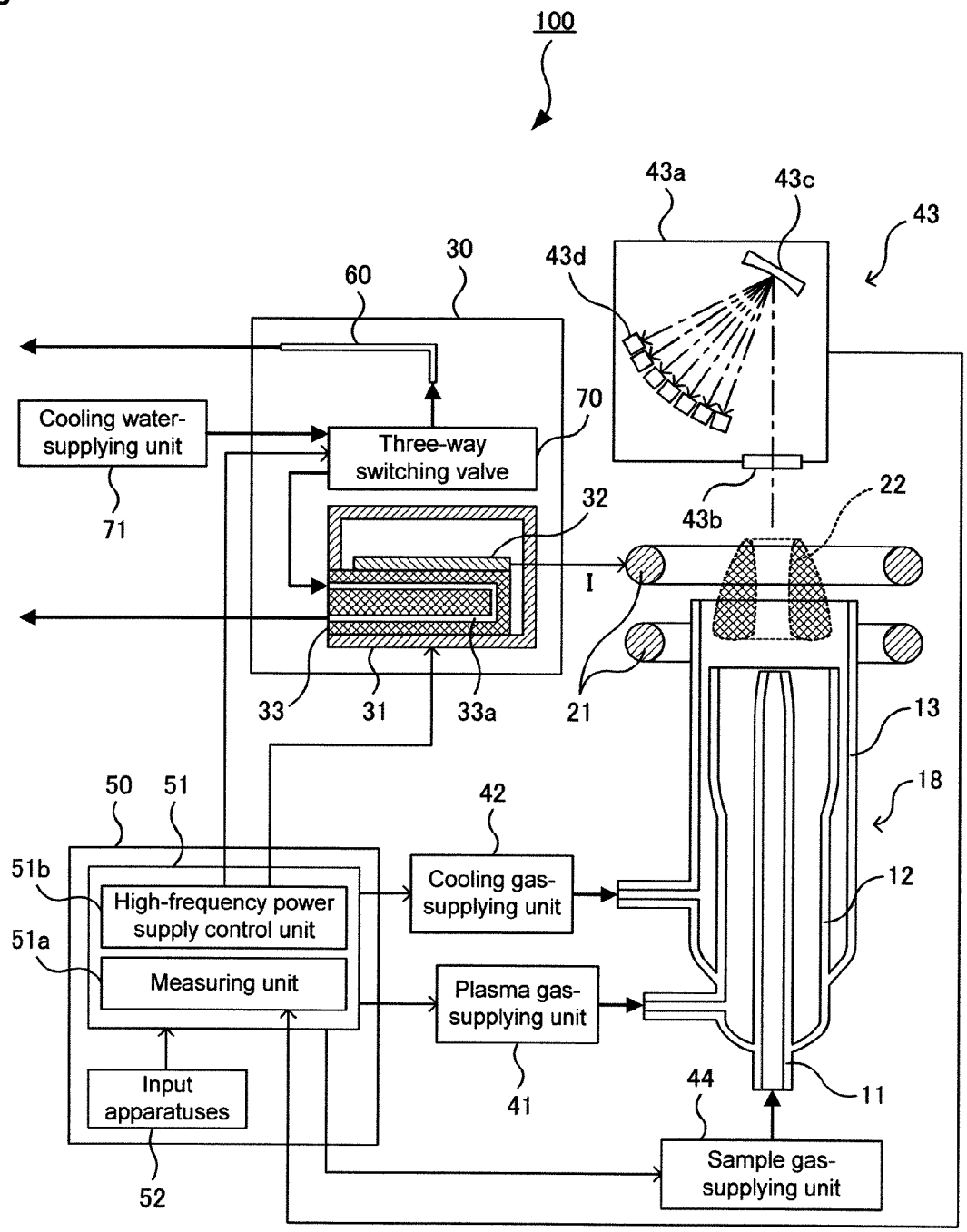
FIG. 1 is a schematic diagram showing the structure of the ICP optical emission spectrometer according to an embodiment.
Figure 2:
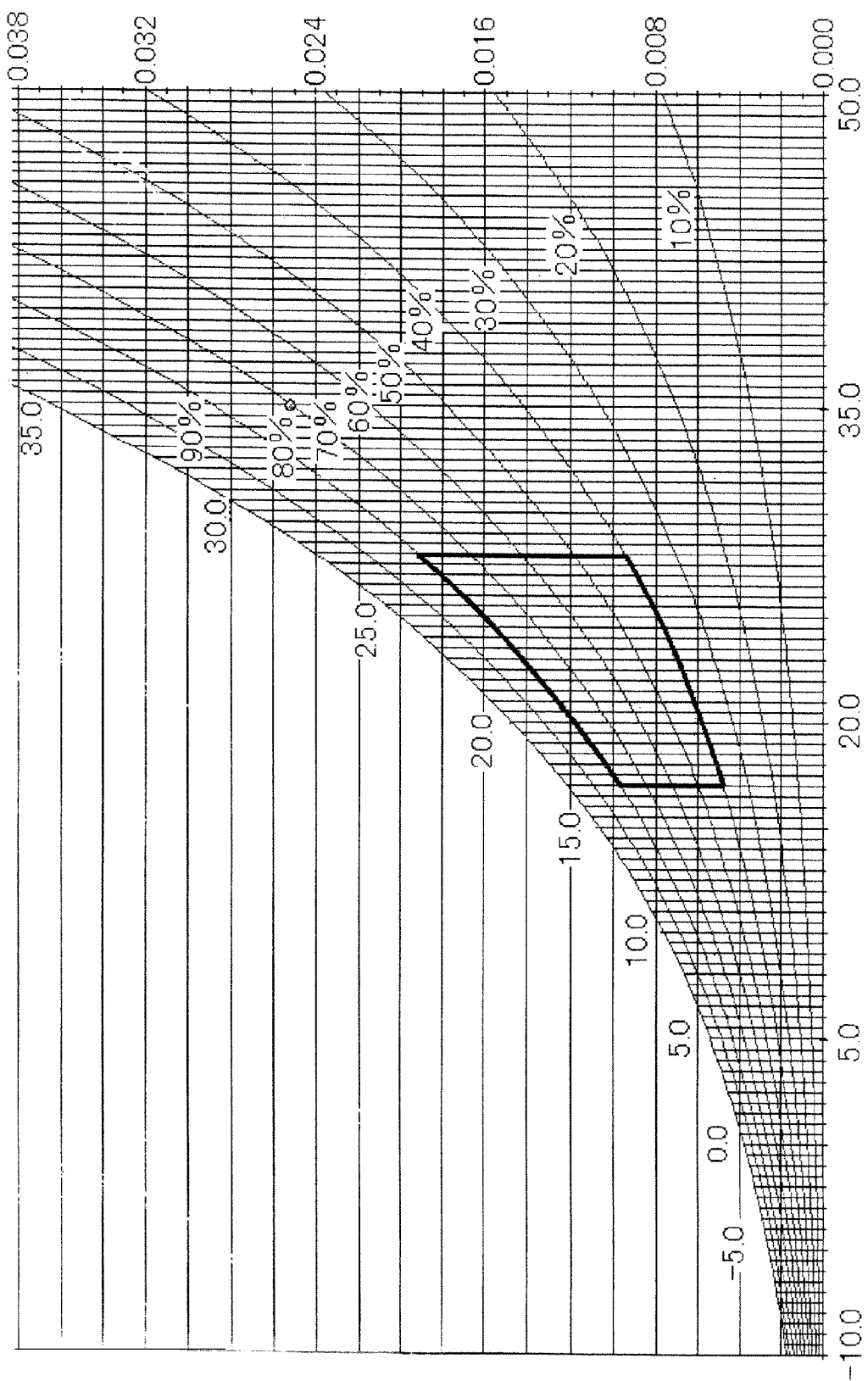
FIG. 2 is a graph showing an air line diagram.
Figure 3:
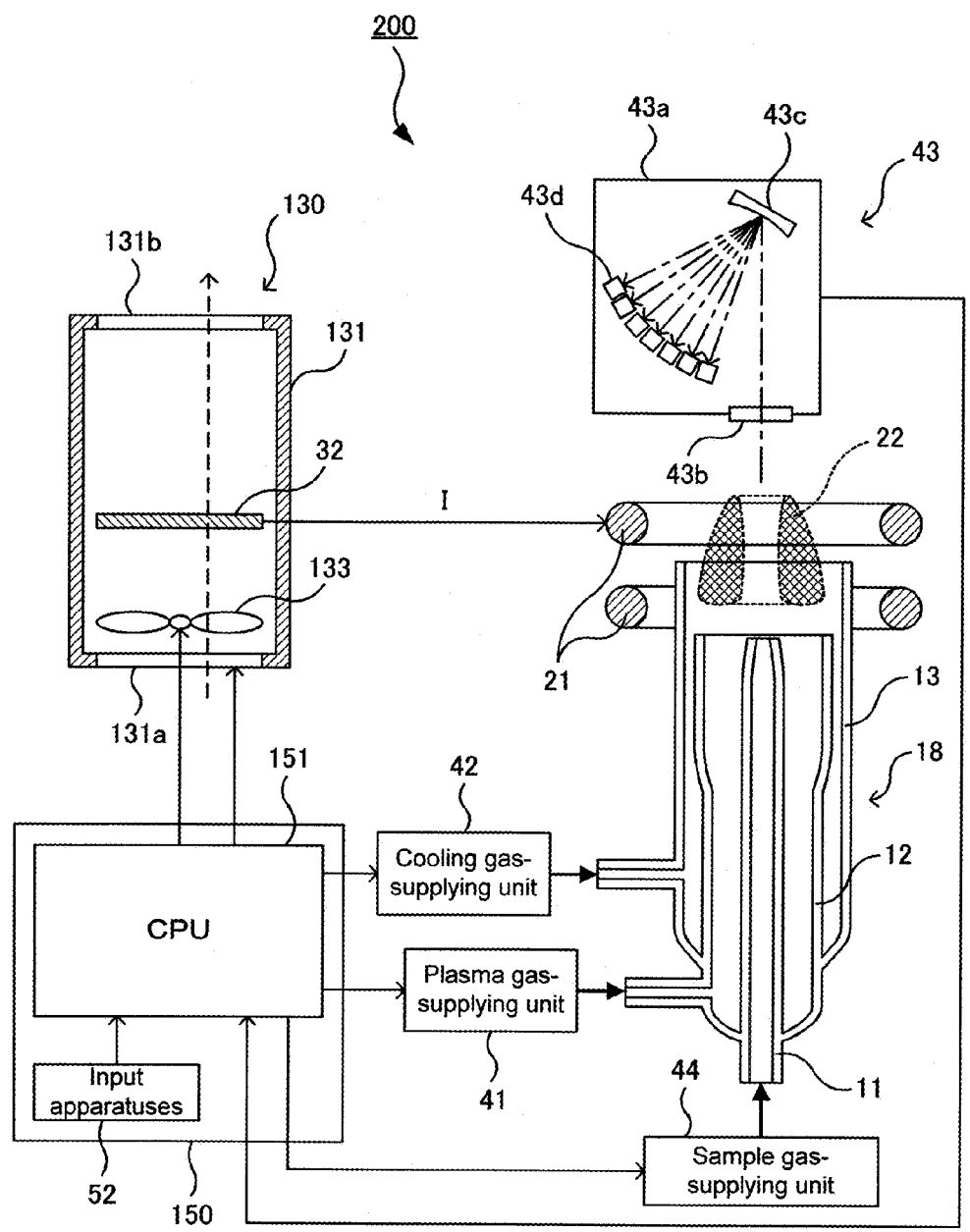
FIG. 3 is a schematic diagram showing the structure of one example of a conventional ICP optical emission spectrometer.

FIG. 1 is a schematic diagram showing the structure of the ICP optical emission spectrometer according to an embodiment. Here, the same symbols are attached to the same or similar components as in the ICP optical emission spectrometer 200.

An ICP optical emission spectrometer 100 is provided with a plasma torch 18 for emission spectrometry that generates a plasma flame 22, a sample gas-supplying unit 44, a plasma gas-supplying unit 41, a cooling gas-supplying unit 42, a light-measuring unit 43 for detecting emitted light, a high-frequency power supply 30 for plasma that supplies a high-frequency current I, and a computer (control unit) 50 for controlling the entirety of the ICP optical emission spectrometer 100.

The high-frequency power supply 30 for plasma is provided with a housing 31 that is sealed airtight, a high-frequency circuit substrate 32 placed inside the housing 31, a cooling copper block 33 placed inside the housing 31, a bypass 60 placed outside the housing 31, and a three-way switching valve (switching mechanism) 70.

The housing 31 is in rectangular parallelepiped form (30 cm×30 cm×30 cm, for example) having an inside space, which is sealed airtight. That is to say, no dust enters into the housing 31.

The cooling copper block 33 is a rectangular parallelepiped (15 cm×15 cm×5 cm, for example) where a coolant path 33a for allowing cooling water (coolant) to flow through is formed so as to wind through the inside. The inlet of the flow path and the outlet of the flow path are formed on one side of the coolant copper block 33. In addition, the upper surface of the cooling copper block 33 makes contact with the lower surface of the high-frequency circuit substrate 32 in the arrangement. The thus-formed cooling copper block 33 is cooled when cooling water (5° C. to 30° C., for example) flows through the coolant path 33a, and furthermore, the high-frequency circuit substrate 32 is cooled, and thus, the elements mounted on the high-frequency circuit substrate 32 are cooled.

The three-way switching valve 70 is connected to the inlet of the flow path of the cooling copper block 33, the inlet of the flow path of the bypass 60, and the cooling water-supplying unit 71. In addition, the three-way switching valve 70 can allow the cooling water supplied from the cooling water-supplying unit 71 to be led into either the inlet of the flow path of the cooling copper block 33 or the inlet of the flow path of the bypass 60. This three-way switching valve 70 is controlled by the computer 50 in accordance with a predetermined timing.

The computer (control unit) 50 is a general purpose computer, and the hardware thereof is formed of a CPU 51 and input apparatuses 52, such as a keyboard and a mouse, that can be illustrated as blocks for the purpose of description. Moreover, the CPU 51 has a measuring unit 51a for carrying out qualitative analysis and quantitative analysis on the basis of the emission spectrum and a high-frequency power supply control unit 51b when the functions processed by the CPU 51 are illustrated as blocks for the purpose of description.

The high-frequency power supply control unit 51b controls the high-frequency circuit substrate 32 together with the three-way switching valve 70 on the basis of the input signal from the input apparatuses 52.

Concretely, when an operator inputs the input signal "turn on plasma" from the input apparatuses 52, a high-frequency current I is supplied from an element on the high-frequency circuit substrate 32 to the high-frequency inductive coil 21, and at the same time, the three-way switching valve 70 is used to allow the cooling water to flow through the coolant path 33a of the cooling copper block 33. That is to say, cooling water flows through the coolant path 33a of the cooling copper block 33 in sync with the turning on of plasma. As a result, the cooling copper block 33 can cool the elements on the high-frequency circuit substrate 32 even though the elements on the high-frequency circuit substrate 32 emit heat.

Meanwhile, when an operator inputs an input signal "turn off plasma" from the input apparatuses 52, the supply of a high-frequency current I to the high-frequency inductive coil 21 from an element on the high-frequency circuit substrate 32 is stopped, and at the same time, the three-way switching valve 70 is used to allow cooling water to flow through the bypass 60. That is to say, cooling water flows through the bypass 60 in sync with the turning off of the plasma. As a result, when no elements on the high-frequency circuit substrate 32 emit heat, the cooling copper block 33 does not cool the elements on the high-frequency circuit substrate 32, and thus, no moisture contained in the air inside the housing 31 forms dew.

As described above, in the ICP optical emission spectrometer 100 according to the present invention, no dust or the like adheres to the elements on the high-frequency circuit substrate 32 and there is no dew condensation, and thus, the elements on the high-frequency circuit substrate 32 can be prevented from short circuiting. In addition, the operation can be automated by the computer 50 in sync with the turning on/off of the plasma.

INDUSTRIAL APPLICABILITY

The present invention can be applied to ICP optical emission spectrometers and the like.

EXPLANATION OF SYMBOLS 18 plasma torch for emission spectrometry
21 high-frequency inductive coil
22 plasma flame
30 high-frequency power supply for plasma
31 housing
32 high-frequency circuit substrate
33 cooling copper block (cooling block)
33a coolant path

What is claimed is:

1. A high-frequency power supply for plasma, comprising:
   a housing;
   a high-frequency circuit substrate placed inside the housing;
   a circuit element, mounted on the high-frequency circuit substrate, for supplying a high-frequency current to a high-frequency inductive coil disposed outside the housing;
   a cooling block for cooling the high-frequency circuit substrate; and
   a coolant path, formed inside the cooling block, for allowing a coolant to flow through inside the cooling block,
   wherein the coolant flows through the coolant path when a high-frequency current is supplied and the coolant does not flow through the coolant path when a high-frequency current is not supplied.

2. The high-frequency power supply for plasma according to claim 1, wherein the inside of the housing is sealed airtight.

3. The high-frequency power supply for plasma according to claim 2, wherein:
   the high-frequency power supply for plasma further comprises a bypass placed outside the housing and a switching mechanism that makes switching between the coolant path and the bypass, and
   the coolant flows through the coolant path when a high-frequency current is supplied and the coolant flows through the bypass when a high-frequency current is not supplied.

4. The high-frequency power supply for plasma according to claim 1, wherein:
the high-frequency power supply for plasma further comprises a bypass placed outside the housing and a switching mechanism that makes switching between the coolant path and the bypass placed, and
the coolant flows through the coolant path when a high-frequency current is supplied and the coolant flows through the bypass when a high-frequency current is not supplied.

5. The high-frequency power supply for plasma according to claim 1, wherein the circuit element includes a transistor and a capacitor.

6. An ICP optical emission spectrometer, comprising:
a high-frequency power supply for plasma;
a plasma torch having a high-frequency inductive coil;
a light-measuring unit for detecting emitted light; and
a control unit for analyzing an element by generating a plasma flame using the plasma torch and introducing a sample into the plasma flame, wherein:
the high-frequency power supply for plasma comprises:
a housing;
a high-frequency circuit substrate placed inside the housing;
a circuit element, mounted on the high-frequency circuit substrate, for supplying a high-frequency current to the high-frequency inductive coil disposed outside the housing;
a cooling block for cooling the high-frequency circuit substrate; and
a coolant path, formed inside the cooling block, for allowing a coolant to flow through inside the cooling block, and
the control unit controls the high-frequency power supply such that the coolant flows through the coolant path when a high-frequency current is supplied to the high-frequency inductive coil and the coolant does not flow through the coolant path when a high-frequency current is not supplied to the high-frequency inductive coil.

7. The ICP optical emission spectrometer according to claim 6, wherein
the inside of the housing is sealed airtight.

8. The ICP optical emission spectrometer according to claim 6, wherein:
the high-frequency power supply for plasma further comprises a bypass placed outside the housing and a switching mechanism that makes switching between the coolant path and the bypass, and
the coolant flows through the coolant path when a high-frequency current is supplied and the coolant flows through the bypass when a high-frequency current is not supplied.

9. The ICP optical emission spectrometer according to claim 6, wherein the circuit element includes a transistor and a capacitor.

10. A high-frequency power supply for plasma, comprising:
a housing;
a high-frequency circuit substrate placed inside the housing;
a circuit element, mounted on the high-frequency circuit substrate, for supplying a high-frequency current to a high-frequency inductive coil disposed outside the housing;
a cooling system for cooling the high-frequency circuit substrate; and
a controller,
wherein the controller is configured to control the cooling system so as to prevent moisture contained in an air inside the housing from forming dew when a high-frequency current is not supplied to the high-frequency inductive coil.

* * * * *